United States Patent [19]

Burg et al.

[11] Patent Number: 4,667,519

[45] Date of Patent: May 26, 1987

[54] RHEOMETER RHELOGICAL/VISCOELASTIC MEASURING APPARATUS AND TECHNIQUE

[75] Inventors: Gary R. Burg, Tyler, Tex.; William T. Prewitt, Tallmadge; James A. Vandyke, Akron, both of Ohio

[73] Assignee: The Goodyear Tire & Rubber Company, Akron, Ohio

[21] Appl. No.: 799,013

[22] Filed: Nov. 18, 1985

[51] Int. Cl.$^4$ ............................................. G01N 3/32
[52] U.S. Cl. ..................................................... 73/815
[58] Field of Search ................ 73/843, 815, 763, 791, 73/59, 811, 814; 364/476, 556

[56] References Cited

U.S. PATENT DOCUMENTS

| Re. 26,562 | 4/1969 | Beatty et al. | 73/815 |
| 3,681,980 | 8/1972 | Decker | 73/815 |
| 3,982,427 | 9/1976 | Decker | 73/815 |
| 4,546,438 | 10/1985 | Prewitt et al. | 73/815 |

Primary Examiner—Stewart J. Levy
Assistant Examiner—Robert R. Raevis
Attorney, Agent, or Firm—T. P. Lewandowski

[57] ABSTRACT

Apparatus and a method for generating data for measuring rheological/viscoelastic properties of curing rubber samples. A stressing mechanism having a variable displacement including a maximum displacement causes variable stress in a curing rubber sample. A measuring mechanism generates measurements of instantaneous stress in the rubber sample while curing, on command. A timer mechanism senses maximum displacement and generates both a maximum displacement signal and a time interval passage signal. The time interval passage signal occurs upon passage of a time interval after maximum displacement. A controller receives and acts upon the maximum displacement signal and the time interval passage signal to command the measuring mechanism to measure instantaneous stress corresponding to maximum displacement and instantaneous stress corresponding to passage of the time interval.

20 Claims, 3 Drawing Figures

RHEOMETER RHELOGICAL/VISCOELASTIC MEASURING APPARATUS AND TECHNIQUE

BACKGROUND OF THE INVENTION

This invention relates to apparatus and methods for generating data for the measurement of rheological and viscoelastic properties of curing rubber samples.

Rheological and viscoelastic properties of curing rubber samples are known to be important to the uses of rubber from which such samples are taken. Several important properties are known in relation to the testing of curing rubber samples for stress as measured by oscillating disc cure rheometers. Such properties include peak strain; viscous modulus, a rheological property of rubber before the cure reaction begins, and loss modulus, a viscoelastic property of substantially completely cured rubber, both designated G''; elastic modulus, the record of stress values divided by peak strain before the cured reaction begins and known as G'; the storage modulus, equivalent to elastic modulus for substantially completely cured rubber and also designated G'; complex modulus, calculated according to the equation $$G^* = \sqrt{(G')^2 + (G'')^2};$$

dynamic viscosity calculated according to the equation $N^* = G''/W$, where W = frequency of oscillation of stress testing; and tangent $\delta$, calculated according to the equation tangent $\delta = G''/G'$.

Prior to the invention, the generation of data for the measurement of the foregoing and other rheological and viscoelastic properties of curing rubber samples required three different samples to be testd on two different types of machines to obtain similar parameters.

SUMMARY OF THE INVENTION

An object of the inventors in the making of this invention was the generation of data for measuring rheological and viscoelastic properties of curing rubber samples in a manner vastly more efficient than that required by the prior art.

In a principal aspect, the invention is an apparatus for generating data for measuring rheological/viscoelastic properties of a curing rubber sample. The apparatus comprises a plurality of means including a stressing means, a measuring means, a timer means, and a controlling means. The stressing means has a variable displacement including a maximum displacement. The purpose of the stressing means is to cause variable stress in the curing rubber sample. The measuring means generates measurements of instantaneous stress in the rubber sample while curing. The measuring means generates such measurements upon command. The purpose of the timer means is to sense maximum displacement and generate two signals. The two signals are a maximum displacement signal and a time interval passage signal. The time interval passage signal is caused to occur upon passage of a time interval after maximum displacement. The controlling means receives and acts upon the maximum displacement signal and the time interval passage signal. The controlling means acts upon such signals to command the measuring means to measure instantaneous stress corresponding to maximum displacement and instantaneous stress corresponding to passage of the time interval.

These and other principal aspects, objects and advantages of the invention will be most clearly understood from a reading of the detailed description of the preferred embodiment of the invention, which follows a brief description of the drawings.

BRIEF DESCRIPTION OF THE DRAWING

The preferred embodiment of the invention will be described in relation to the accompanying drawing. The accompanying drawing includes three figures. Each figure is briefly described as follows.

DETAILED DESCRIPTION OF THE PREFERRED EMBODIMENT

Figure 1:
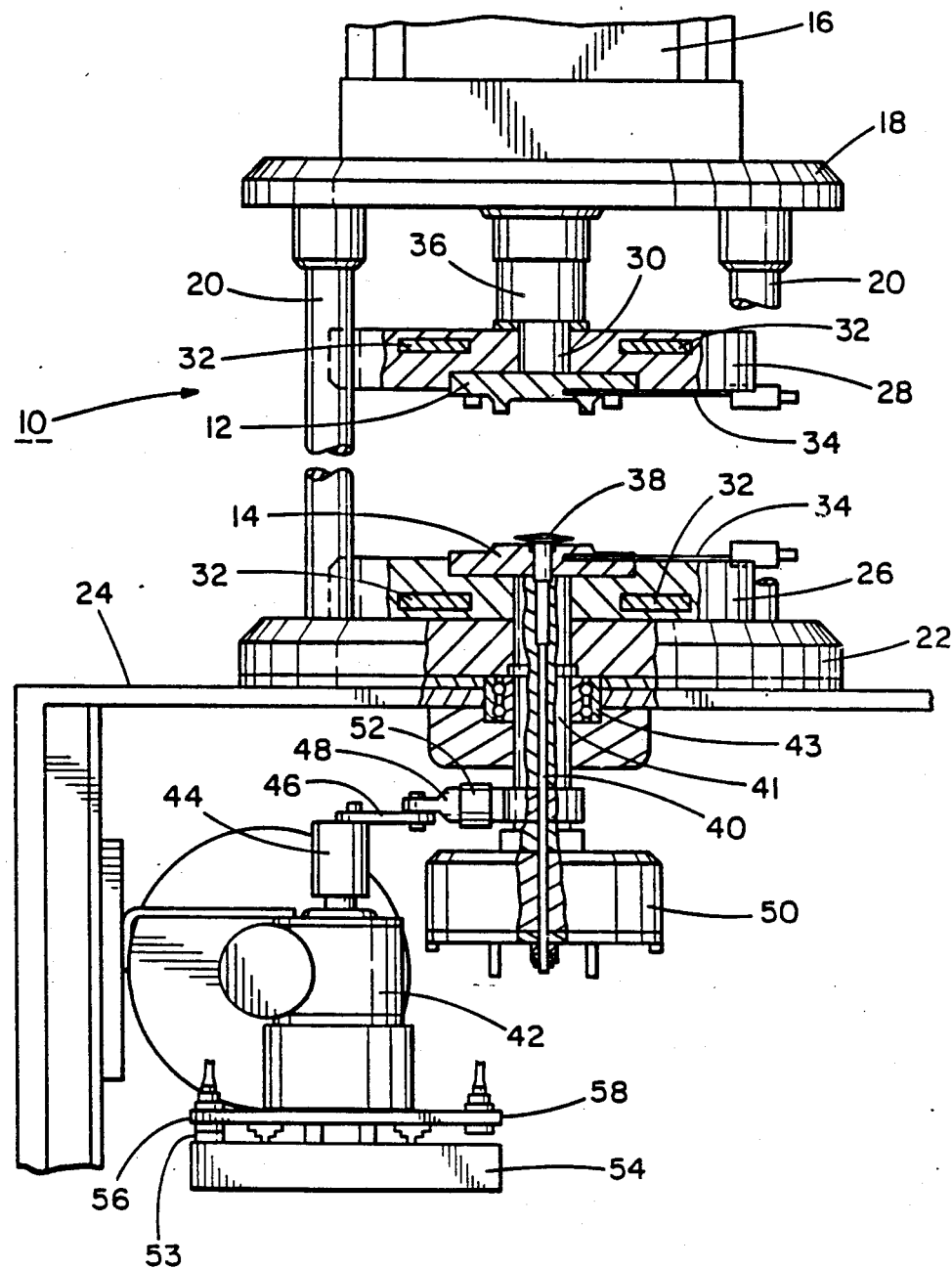
FIG. 1 is a schematic view of the components of a rheometer.

Referring to FIG. 1, the preferred apparatus comprises, in part, a rheometer 10 having an upper die 12 and a lower die 14 defining a die cavity for rubber samples (not shown). Samples are successively loaded in the die cavity, which is closed by lowering the upper die 12 through operation of a pneumatic cylinder 16.

The cylinder 16 is supported atop a frame plate 18 and underlying frame rods 20. The rods 20 extend from a rod base 22 atop a base support 24. The lower die 14 rests on a lower heating platen 26, which rests on the base 22. The upper die 12 is mounted to the underside of an upper heating platen 28, which is mounted to the rod 30 of the cylinder 16.

The platens 26, 28 include embedded electrical heaters 32. The dies 12, 14 include heat probes 34. A rod insulator 36 protects the rod 30 from heat.

The heaters 32 heat the platens 26, 28, dies 12, 14 and any sample in the die cavity. The probes 34 provide feedback for accurate control of the heaters 32, and accurate heating of samples.

A biconical disc 38 of a rotor projects into the die cavity. The disc 38 is mounted atop an oscillatory rotor shaft 40, which projects through the lower die 14, lower platen 26, rod base 22 and base support 24. The rotor shaft 40 is pneumatically clamped by a pneumatic clamping mechanism 50. The shaft 40 is rotatably mounted to the base support 24 within a shaft support 41 and bearing 43. The shaft 40 and disc 38 are oscillated by a main, line synchronous motor and gear box 42 mounted to the base support 24. The main motor and gear box 42 drive an eccentric 44. The eccentric 44 rotates, and rotates the attached end of a link arm 46. The other end of the link arm 46 oscillates a torque arm 48 and the shaft 40. The rotor is oscillated through an arc of a few degrees, preferably at 100 cycles per minute as determined by the motor and gear box 42.

Figure 2:
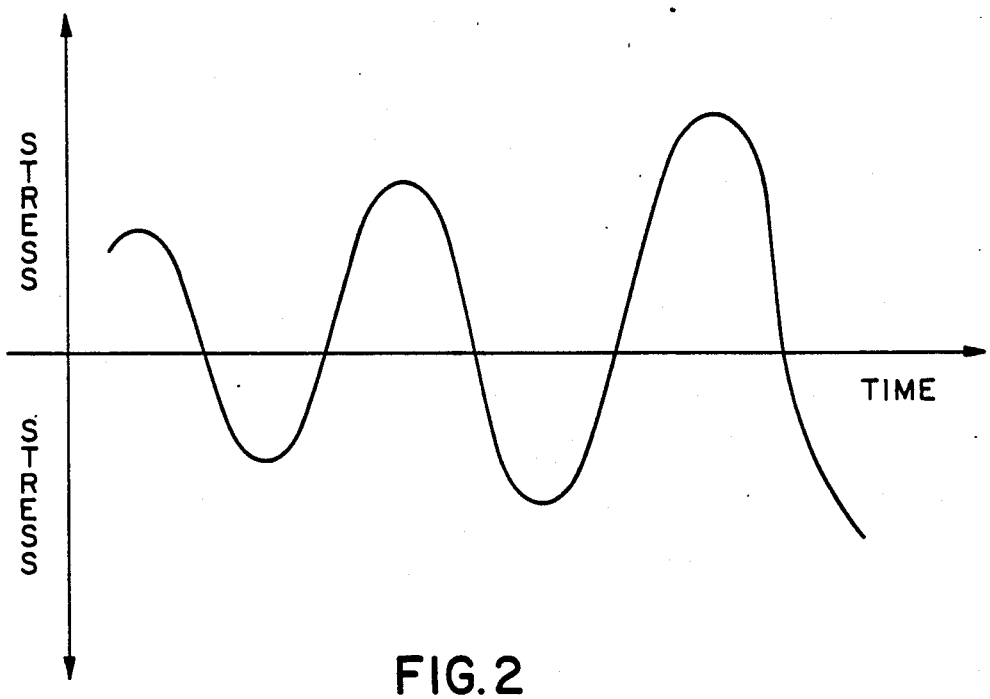
FIG. 2 is a stress vs. time diagram of the stress which occurs in a curing rubber sample during curing in a rheometer as in FIG. 1.

A torque arm transducer, such as the strain gauge 52, measures the torque upon or strain in the torque arm 48. The strain in the torque arm 48 is representative of, and more specifically, proportional to, the torque upon the arm 48, arising from the resistance of the sample to the oscillation of the rotor. The resistance arises from and increases with cross-linking occurring within the rubber as it cures. Thus, the gauge 52 measures the strain upon the rotor, which is proportional to the torque of the resisting rubber samples. The torque applied to the rotor causes a change in the voltage of the transducer proportional to the torque arising from the sample resisting oscillation of the rotor. The frequency of the torque signal is 100 cycles per minute, corresponding to the frequency of rotor oscillation. Referring to FIG. 2, the analog signal generated by strain gauge 52 appears when graphed in relation to time as an alternating sinusoidal signal of increasing magnitude. Magnitude increases as the rubber sample cures due to increased resistance of the sample to the motion of the rotor.

Referring again to FIG. 1, a magnet 53 is mounted on a magnet wheel 54. The wheel 54 is connected for rotation with the eccentric 44. A pair of Hall Effect switches 56, 58 are affixed to the motor 42 and thereby the base support 24. The switches 56, 58 are positioned relative to the magnet on the wheel 54 and the eccentricity of the eccentric 44 so as to provide accurate indications of the times of occurrence of maximum displacements among the variable displacements of the disc 38.

Figure 3:
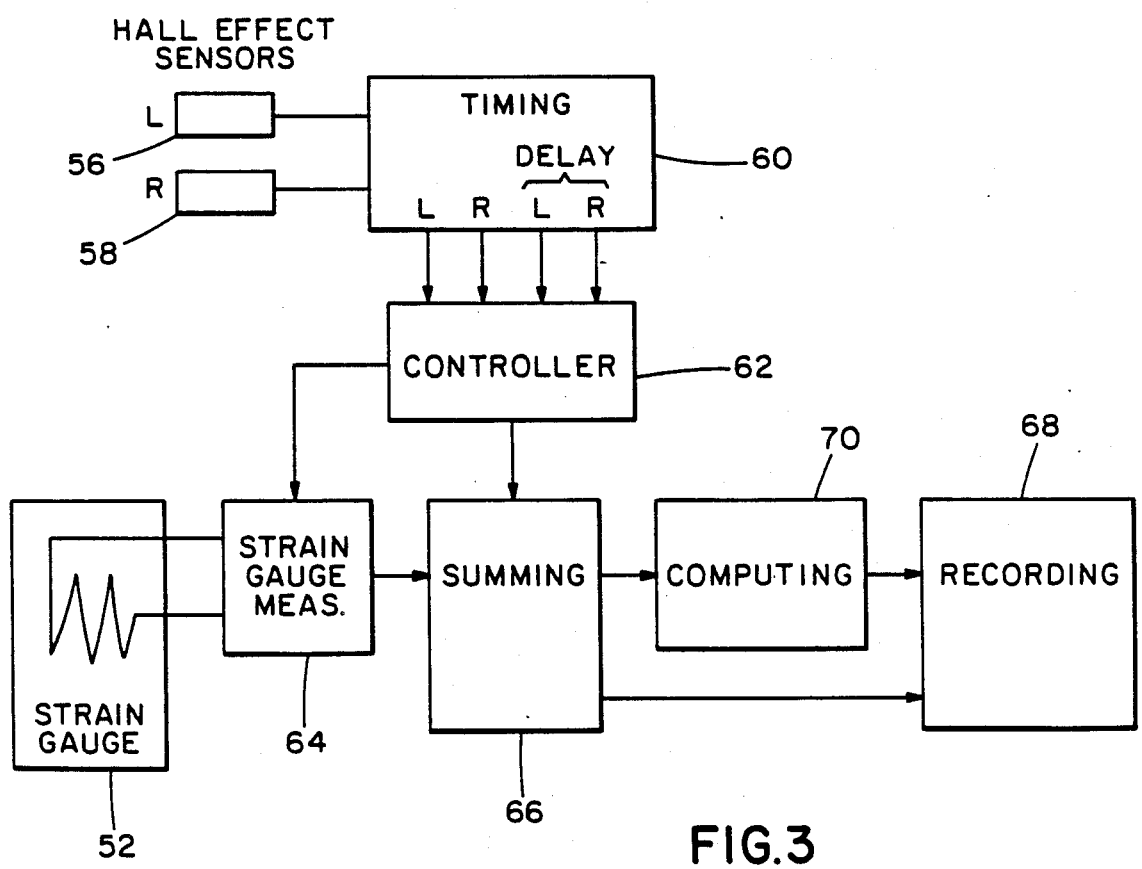
FIG. 3 is a block diagram of the preferred embodiment of the invention.

Referring to FIG. 3, the preferred apparatus also includes a digital electronic timer 60. The timer 60 is operatively electrically connected to the Hall Effect switches 56, 58. The timer 60 is so connected to receive from the switches 56, 58 the indications of times of occurrence of maximum displacements of the disc 38. The timer 60 also includes an internal clock. Receipt of an indication of disc maximum displacement initiates or starts the clock function toward a pre-set maximum. The pre-set maximum equals half or some other ratio of the time interval from the closure of one switch 56 (or 58) to the closure of the other switch 58 (or 56). The preset maximum is recalculated every time another pair of time measurements 56, 58 or 58,56 is known.

The timer 60 is operatively electrically connected to a digital electronic controller 62 and generates signals thereto. The timer 60 generates a maximum displacement signal upon closure of the left Hall Effect switch 56, a time interval passage signal upon passage of the pre-set maximum time interval thereafter, a maximum displacement signal upon closure of the right switch 58, and a time interval passage signal thereafter. As the switch closures repeat, the timer signals repeat. The clock of the timer 60 re-sets after each time interval passage signal.

The controller 62 is operatively electrically connected to a strain gauge measuring component 64 and a summing component 66. The strain gauge measuring component 64 is operatively electrically connected to the strain gauge 52. The controller 62 triggers the strain gauge measuring component 64 to generate an instantaneous reading of stress from the strain gauge 52 upon the occurrence of each maximum displacement signal and each time interval passage signal. The measuring component 64 is operatively electrically connected to the summing component 66 and generates the stress readings to the summing component 66.

The summing component 66 is an electronic, microprocessor based computer. The readings from the strain gauge measuring component 64 are manipulated to form the absolute value $AVS_{max}$ of the sum of each successive pair of measurements of instantaneous stress corresponding to maximum displacement. The readings are further manipulated to form the absolute value $AVS_{int}$ of the sum of each successive pair of measurements of instantaneous stress corresponding to passage of the time interval.

A recorder 68 receives the absolute values of the summing component 66, as does a computing component 70. The recorder 68 records the absolute values.

The computing component 70 computes a variety of rheological/viscoelastic properties from the absolute values. First, elastic or storage modulus G' is computed foe each absolute value $AVS_{max}$ according to the equation $$G' = (AVS_{max}/X)$$

where X is the maximum percent strain in a sample. X is fixed by chamber and rotor geometry. Second, viscous or loss modulus is computed for each absolute value $AVS_{int}$ according to the equation $$G'' = (AVS_{int}/X)$$

Third, for each succeeding pair of G' and G'', the complex modulus G* is computed. Fourth, for each succeeding pair G' and G'', tangent $\delta$ is computed. All computed rheological/viscoelastic properties are transmitted to the recorder 68, which records each property G', G'', G* and tangent $\delta$ for each corresponding pair of absolute values $AVS_{max}$ and $AVS_{int}$.

The invention, and the manner and process of making and using it, are now described in such full, clear, concise and exact terms as to enable any person skilled in the art to which it pertains, to make and use the same. It is to be understood, of course, that the foregoing describes a preferred embodiment of the present invention and that modifications may be made therein without departing from the spirit or scope of the present invention as set forth in the claims. As examples, the components of the preferred embodiment constitute one form of various means plus function elements in which the invention may be embodied. To particularly point out and distinctly claim the subject matter regarded as invention, the following claims conclude this specification.

What is claimed is:

1. Apparatus for generating data for measuring rheological/viscoelastic properties of a curing rubber sample, the apparatus comprising:
   stressing means having a variable displacement including a maximum displacement for causing variable stress in the curing rubber sample;
   measuring means for generating measurements of instantaneous stress in the rubber sample when curing, on command;
   means for sensing maximum displacement and generating both a maximum displacement signal and a time interval passage signal, the time interval passage signal occurring upon passage of a time interval after maximum displacement;
   controlling means for receiving and acting upon the maximum displacement signal and the time interval passage signal to command the measuring means to measure instantaneous stress corresponding to maximum displacement and instantaneous stress corresponding to passage of the time interval.

2. Apparatus as in claim 1 further comprising:
   summing means for forming the absolute value of the sum of the instantaneous stress corresponding to maximum displacement and the instantaneous stress corresponding to passage of the time interval, to generate a summed stress value.

3. Apparatus as in claim 2 further comprising:
   recording means for recording the summed stress value.

4. Apparatus as in claim 1 further comprising:

computing means for computing the ratio of the instantaneous stress corresponding to passage of the time interval to the instantaneous stress corresponding to maximum displacement.

5. Apparatus as in claim 1 further comprising rheometer means for causing the curing of the rubber sample, the rheometer including the stressing means and the measuring means.

6. Apparatus as in claims 1 or 5 in which the stressing means includes a motor driven oscillating rotor.

7. Apparatus as in claims 1 or 5 in which the measuring means includes strain gauges affixed to the stressing means for measuring strain in the stressing means.

8. Apparatus as in claim 1 in which the timer means and controlling means are digital electronic equipment.

9. Apparatus as in claim 1 in which stressing means constitutes a stressing means having a variable displacement including a series of maximum displacements;
in which the timer means constitutes timer means for sensing a plurality of maximum displacements in the series of maximum displacements and generating both a maximum displacement signal and a time interval passage signal for each of the plurality of maximum displacements; and
in which the controlling means constitutes controlling means for receiving and acting upon each maximum displacement signal and each time interval passage signal.

10. Apparatus as in claim 9 further comprising:
summing means for forming the absolute value of the sum of each instantaneous stress corresponding to maximum displacement and the next instantaneous stress corresponding to passage of the time interval, to generate a plurality of summed stress values.

11. Apparatus as in claim 10 in which the summing means further constitutes means for forming the absolute value of the difference between pairs of successive instantaneous stresses corresponding to maximum displacement.

12. Apparatus for generating data for measuring rheological/viscoelastic properties of a curing rubber sample, the apparatus comprising:
stressing means having a variable displacement including a series of maximum displacements for causing variable stress in the curing rubber sample;
measuring means for generating measurements of instantaneous stress in the rubber sample when curing, on command;
timer means for sensing a plurality of maximum displacement in the series of maximum displacements and generating both a maximum displacement signal and a time interval passage signal for each of the plurality of maximum displacements, the time interval passage signal occuring upon passage of a time interval after maximum displacement;
controlling means for receiving and acting upon each maximum displacement signal and each time interval passage signal to command the measuring means to measure instantaneous stress corresponding to each of the plurality of maximum displacements and instantaneous stress corresponding to passage of a time interval after each of the plurality of maximum displacements;
summing means for forming the absolute value of the sum of each instantaneous stress corresponding to maximum displacement and the instantaneous stress corresponding to passage of the time interval thereafter, to generate a plurality of summed stress values;
recording means for recording the summed stress values; and
computing means for computing the ratios of the instantaneous stresses corresponding to passage of the time interval to the instantaneous stresses corresponding to maximum displacement.

13. Apparatus as in claim 12 further comprising rheometer means for causing the curing of the rubber sample, the rheometer including the stressing means and the measuring means;
the stressing means including a motor driven oscillating rotor,
the measuring means including strain gauges affixed to the stressing means for measuring strain in the stressing means,
and the timer means and controlling means being digital electronic equipment.

14. A method of generating data for measuring rheological/viscoelastic properties of a curing rubber sample, the method comprising:
causing variable stress in the curing rubber sample at variable displacements including a maximum displacement;
sensing maximum displacement and generating both a maximum displacement signal and a time interval passage signal, the time interval passage signal occuring upon passage of a time interval after maximum displacement; and
acting upon the maximum displacement signal and the time interval passage signal to generate measurements of instantaneous stress corresponding to maximum displacement and instantaneous stress corresponding to passage of the time interval.

15. A method as in claim 14 further comprising:
forming the absolute value of the sum of the instantaneous stress corresponding to maximum displacement and the instantaneous stress corresponding to passage of the time interval, to generate a summed stress value.

16. A method as in claim 14 further comprising:
recording the summed stress value.

17. A method as in claim 14 further comprising:
computing the ratio of the instantaneous stress corresponding to passage of the time interval to the instantaneous stress corresponding to maximum displacement.

18. A method for generating data for measuring rheological/viscoelastic properties of a curing rubber sample, the method comprising:
causing variable stress in the curing rubber sample at variable displacements including a series of maximum displacements;
sensing a plurality of maximum displacements in the series of maximum displacements and generating both a maximum displacement signal and a time interval passage signal for each of the plurality of maximum displacements, each time interval passage signal occuring upon passage of a time interval after a maximum displacement; and
acting upon each maximum displacement signal and each time interval passage signal to generate measurements of instantaneous stress corresponding to maximum displacement and instantaneous stress corresponding to passage of the time interval.

19. A method as in claim 18 further comprising:

forming the absolute value of the sum of each instantaneous stress corresponding to maximum displacement and the instantaneous stress corresponding to passage of the time interval thereafter, to generate a plurality of summed stress values.

20. A method as in claim 18 further comprising:
recording the summed stress values; and
computing the ratios of each instantaneous stress corresponding to passage of the time interval to the immediately preceding instantaneous stress corresponding to maximum displacement.

* * * * *